United States Patent
O'Brien et al.

(10) Patent No.: US 10,695,035 B2
(45) Date of Patent: Jun. 30, 2020

(54) SYSTEMS AND METHODS FOR ASSESSING SIGNAL QUALITY

(71) Applicant: Neural Analytics, Inc., Los Angeles, CA (US)

(72) Inventors: Michael O'Brien, Los Angeles, CA (US); Mina Ranjbaran, Los Angeles, CA (US); Robert Hamilton, Los Angeles, CA (US); Samuel G. Thorpe, Los Angeles, CA (US); Nicolas Canac, Los Angeles, CA (US)

(73) Assignee: Neural Analytics, Inc., Los Angeles, CA (US)

(*) Notice: Subject to any disclaimer, the term of this patent is extended or adjusted under 35 U.S.C. 154(b) by 0 days.

(21) Appl. No.: 16/245,129

(22) Filed: Jan. 10, 2019

(65) Prior Publication Data
US 2019/0209141 A1    Jul. 11, 2019

Related U.S. Application Data

(60) Provisional application No. 62/616,410, filed on Jan. 11, 2018.

(51) Int. Cl.
| | |
|---|---|
| *A61B 8/00* | (2006.01) |
| *A61B 8/08* | (2006.01) |
| *A61B 8/06* | (2006.01) |
| *G01N 29/40* | (2006.01) |
| *G01N 29/46* | (2006.01) |

(Continued)

(52) U.S. Cl.
CPC .............. *A61B 8/58* (2013.01); *A61B 8/06* (2013.01); *A61B 8/0808* (2013.01); *A61B 8/0891* (2013.01); *A61B 8/429* (2013.01); *A61B 8/486* (2013.01); *A61B 8/488* (2013.01); *A61B 8/5207* (2013.01); *A61B 8/5223* (2013.01); *G01N 29/40* (2013.01); *G01N 29/4436* (2013.01); *G01N 29/4445* (2013.01); *G01N 29/4463* (2013.01); *G01N 29/46* (2013.01); *A61B 5/4064* (2013.01); *G01N 2291/02475* (2013.01); *G01N 2291/02483* (2013.01)

(58) Field of Classification Search
None
See application file for complete search history.

(56) References Cited

U.S. PATENT DOCUMENTS

| | | | |
|---|---|---|---|
| 5,648,613 A * | 7/1997 | Kiefer | G01N 29/0672 73/609 |
| 9,414,786 B1 * | 8/2016 | Brockway | A61B 5/7203 |
| 2002/0062086 A1 | 5/2002 | Miele et al. | |

(Continued)

OTHER PUBLICATIONS

International Search Report and Written Opinion dated Apr. 4, 2019, from application No. PCT/US2019/013111.

*Primary Examiner* — Carolyn A Pehlke
*Assistant Examiner* — Marjan Saboktakin
(74) *Attorney, Agent, or Firm* — Foley & Lardner LLP

(57) ABSTRACT

Systems, apparatuses, methods, and non-transitory computer-readable media for assessing signal quality of a signal are described herein, including determining a signal quality assessment (SQA) metric of the signal based on at least one energy function of the signal, determining whether the SQA metric is above a threshold, and in response to determining that the SQA metric is above the threshold, performing additional signal processing of the signal.

29 Claims, 5 Drawing Sheets

(51) Int. Cl.
  *G01N 29/44*   (2006.01)
  *A61B 5/00*   (2006.01)

(56) References Cited

U.S. PATENT DOCUMENTS

2007/0016046 A1\* 1/2007 Mozayeni ................ A61B 8/06
                                                      600/443
2016/0081064 A1   3/2016 Kwak et al.
2017/0188992 A1\* 7/2017 O'Brien ............... A61B 8/0891

\* cited by examiner

SYSTEMS AND METHODS FOR ASSESSING SIGNAL QUALITY

CROSS-REFERENCE TO RELATED PATENT APPLICATIONS

The present disclosure claims priority to, and the benefit of, U.S. provisional patent application Ser. No. 62/616,410, titled QUANTITATIVE ULTRASOUND SIGNAL QUALITY ASSESSMENT, and filed on Jan. 11, 2018, which is incorporated herein by reference in its entirety.

BACKGROUND

Ultrasound (e.g., transcranial Doppler ultrasound (TCD)) is a powerful diagnostic tool for a number of pathologies including but not limited to, vasospasm, high intracranial pressure, acute ischemic stroke, mild traumatic brain injury, and so on. Traditional metrics such as mean velocity has been used to assess ultrasound signal quality for decades. However, previous studies have demonstrated that these traditional metrics can vary greatly in inter/intra-sonographer repeated scans. Furthermore, these metrics alone may not provide adequate robustness in accurately determining ultrasound signal quality. Therefore, the traditional metrics such as but not limited to, mean velocity and PI, may not provide sufficient reliability. As such, different metrics may provide more reliability in assessing signal quality when used in addition to, or instead of, the traditional metrics.

SUMMARY

According to various arrangements, there is provided a method for assessing signal quality of a signal from a subject. The method includes determining a signal quality assessment (SQA) metric of the signal of the subject based on at least one energy function of the signal. The method further includes determining whether the SQA metric is above a threshold. The method further includes, in response to determining that the SQA metric is above the threshold, performing additional signal processing of the signal.

In some arrangements, the signal comprises an ultrasound signal.

In some arrangements, the signal includes one or more cerebral blood flow velocity (CBFV) waveforms.

In some arrangements, the method further includes moving the probe to a first location of the subject and receiving, by the probe, the signal from the subject at the first location.

In some arrangements, the first location is at a temporal area of the subject.

In some arrangements, the method further includes determining that the SQA metric is not above the threshold, moving the probe to a second location of the subject in response to determining that the SQA metric is not above the threshold, and configuring the probe to receive additional signal of the second location.

In some arrangements, the method further includes determining that a segment of a first trajectory path of the probe has deteriorating signal quality based on the SQA metric for the segment, wherein the first location is on the first trajectory path. The method further includes moving the probe along a second trajectory path different from the first trajectory path in response to determining that the segment of the first trajectory path has the deteriorating signal quality.

In some arrangements, the method further includes receiving the signal from a signal database, wherein performing the additional signal processing of the signal includes at least one of admitting the signal as a part of a training data set or a testing data set for machine learning algorithms, admitting the signal for testing and training improved diagnostic settings, or admitting the signal for determining improved search algorithms.

In some arrangements, the method further includes disregarding the signal responsive to determining that the SQA metric is not above the threshold.

In some arrangements, the at least one energy function includes M-Mode energy.

In some arrangements, receiving the signal includes receiving the signal in an M-Mode, and the M-Mode energy is determined using the signal received in the M-Mode.

In some arrangements, the at least one energy function includes envelope energy.

In some arrangements, the envelope energy is determined based on a spectrogram of the signal.

In some arrangements, the at least one energy function includes bounded spectral power (BSP) energy.

In some arrangements, the BSP energy is determined based on a spectrogram of the signal.

In some arrangements, the at least one energy function includes High Frequency Ratio (HFR) energy.

In some arrangements, the at least one energy function includes pulsatility index (PI).

In some arrangements, the SQA metric is determined based on at least one of M-Mode energy, envelope energy, bounded spectral power (BSP) energy, or High Frequency Ratio (HFR) energy.

In some arrangements, the threshold is set based on demographic information of the subject.

In some arrangements, the threshold is dynamic.

In some arrangements, the threshold changes over time.

In some arrangements, the threshold starts from an initial value, the threshold increases from the initial value responsive to determining that the initial value is exceeded by the SQA metric, and the threshold decreases from the initial value responsive to determining that the initial value is not exceeded by the SQA metric for a period of time.

In some arrangements, determining the SQA metric includes applying a gating function to the at least one energy function of the signal.

In some arrangements, the gating function includes M-Mode energy.

In some arrangements, determining the SQA metric includes weighting each of the at least one energy function by applying a scalar to each of the at least one energy function of the signal.

In some arrangements, the method further includes receiving user input corresponding to at least one medical condition, the at least one energy function includes a plurality of energy functions, selecting one or more of the plurality of energy functions based on the user input, and determining the SQA metric based on the one or more of the plurality of energy functions.

In some arrangements, performing the additional signal processing of the signal includes at least one of performing beat segmentation for the signal, identifying one or more morphological features of the signal, or displaying the one or more morphological features.

In some arrangements, the method further includes displaying the SQA metric at a display device.

According to various arrangements, there is provided a tool for facilitating medical diagnosis. The tool includes a processing circuit configured to determine a signal quality assessment (SQA) metric for a signal of the subject based on at least one energy function of the signal. The tool is further configured to determine whether the SQA metric is above a threshold. The tool is further configured to, in response to determining that the SQA metric is above the threshold, perform additional signal processing of the signal.

According to various arrangements, there is provided a non-transitory computer-readable medium having computer-readable instructions such that, when executed by a processor, assess signal quality of a signal from a subject by determining a signal quality assessment (SQA) metric for the signal based on at least one energy function of the signal, determining whether the SQA metric is above a threshold, and, in response to determining that the SQA metric is above the threshold, performing additional signal processing of the signal.

BRIEF DESCRIPTION OF THE FIGURES

Features and aspects of the present disclosure will become apparent from the following description and the accompanying example arrangements shown in the drawings, which are briefly described below.

DETAILED DESCRIPTION

Figure 1:
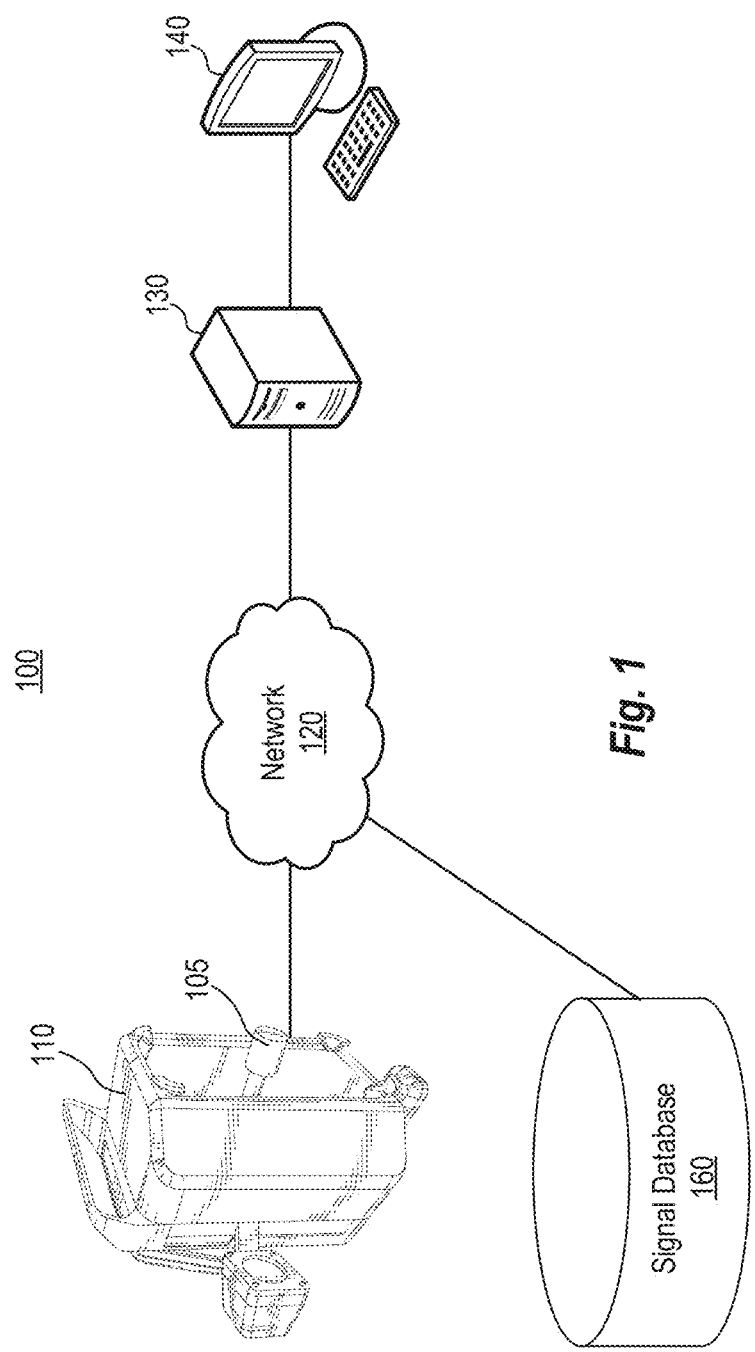
FIG. 1 is a schematic diagram illustrating a system for assessing signal quality according to various arrangements.

The detailed description set forth below in connection with the appended drawings is intended as a description of various configurations and is not intended to represent the only configurations in which the concepts described herein may be practiced. The detailed description includes specific details for providing a thorough understanding of various concepts. However, it will be apparent to those skilled in the art that these concepts may be practiced without these specific details. In some instances, well-known structures and components are shown in block diagram form in order to avoid obscuring such concepts.

In the following description of various arrangements, reference is made to the accompanying drawings which form a part hereof and in which are shown, by way of illustration, specific arrangements in which the arrangements may be practiced. It is to be understood that other arrangements may be utilized, and structural changes may be made without departing from the scope of the various arrangements disclosed in the present disclosure.

Arrangements described herein relate to apparatuses, systems, methods, and non-transitory computer-readable medium for implementing a signal quality assessment (SQA) metric used to assess signal quality of ultrasound signals (e.g., TCD signals). The SQA metric can be used consistently for ultrasound data acquisition and assessment across various sonography platforms. In some examples, the SQA metric as described herein is a metric or function evaluation that quantifies ultrasound signal quality to ensure the ultrasound signals are qualified for morphological feature extraction. For example, based on the SQA metric, one or more signals can be determined to be sufficiently high quality (e.g., above a threshold of the SQA metric) for performing further analysis on the signals (e.g., manual visual analysis or computer-based feature extraction). In some examples, the threshold is dynamic as described herein. In other examples, the threshold is static. In some examples, the threshold can be set based on attributes (e.g., demographic information such as but not limited to, age, race, gender, and so on) of the subject. For example, the threshold can be set to be lower for older subjects, and higher younger subjects. On the other hand, the SQA metric can indicate signals that are relatively low quality such that those signals can be discarded or otherwise not used for further analysis.

Morphological features of ultrasound signal waveforms (e.g., cerebral blood flow velocity (CBFV) waveforms), which may be subtle in nature, provide valuable information about the status of the cerebral vasculature. Therefore, morphological features of ultrasound waveforms can be used to diagnose a number of medical conditions. Further disclosure related to using morphological features of ultrasound waveforms as diagnostic tools can be found in U.S. patent publication no. 2019/0216433, filed May 4, 2018, titled WAVEFORM VISUALIZATION TOOL FOR FACILITATING MEDICAL DIAGNOSIS, which is incorporated herein by reference in its entirety. While being more robust to mean velocity fluctuations, high quality ultrasound signals can be used to analyze precise morphological features for accurate assessment of various pathologies. Therefore, the SQA metric described herein can be a threshold used to determine whether an ultrasound signal exhibits sufficient signal quality to be used for further analysis (e.g., morphological feature extraction and analysis).

In some arrangements, the SQA metric can be referred to as an energy function or an objective function of the ultrasound signal. For example, the SQA metric can be determined based on one or more individual functions. For example, these individual functions can include motion mode or multi-mode (M-Mode) energy (e.g., power or velocity M-Mode), envelope energy, bounded spectral power (BSP) energy, and more as described herein.

In some arrangements, the SQA metric can be defined based on M-Mode energy. Measuring the ultrasound data in M-Mode provides signal velocity or power information at every depth of an anatomic feature (e.g., a brain) of a subject, between a minimum and maximum depth value. Typically, vessel insonation is improved when the probe is lined up parallel to the vessel (e.g., such that a length of the probe, and therefore an ultrasound beam emitted from the probe, is oriented along the same direction as the length of a vessel, and therefore the flow of blood within the vessel). Vessel insonation refers to ultrasound penetration of vessels. For a particular insonation target point (e.g., a particular anatomic feature of interest, such as a particular vessel or a particular point in the brain), vessel insonation can be achieved using the widest M-Mode band. Thus, the M-Mode energy quantifies widths of contiguous M-Mode bands as the contiguous M-Mode bands can be used to determine that a direction of insonation is strongly aligned with the vessel. An additional contributor to the M-Mode energy is power distribution in the M-Mode band. The power distribution distinguishes between two M-Mode energies of the same band width. In some examples, an additional contributor to the M-Mode energy is direction/directional patterns (e.g. all red or red then blue then red). In some examples, an additional contributor to the M-Mode energy is the depth at which the M-Mode band exists. In one instance, the depth for which the MCA overlaps may be at 50 mm. Each of these contributors can factor into the definition of the SQA metric as M-Mode energy is used to calculate the SQA metric.

In some cases, initial scanning by the probe to search for an ultrasound signal typically yields little to no available signal. In such cases, the M-Mode signal may be a signal to obtain and analyze. With respect to searching for a temporal window region of a head of a subject, any activity in the M-Mode signal suggests that the probe is within a temporal window region. Therefore, initial signal analysis attempts (before other signal types can be reliably acquired) using M-Mode energies can reveal useful information regarding signal quality with respect to a particular anatomical feature of interest (e.g., the temporal window region).

Accordingly, the M-Mode energy (or energy function) is a powerful energy function to analyze first. The probe can be configured to collect ultrasound data in the M-Mode over a relatively short data segment (e.g., a relatively short period of data collection time). Therefore, the M-Mode energy can be calculated using data collected over a shorter period of time, and that the robotics can be configured to move the probe more quickly within a workspace of the probe. Although ultrasound (e.g., TCD) signals acquired over a shorter period of time are generally prone to noise and therefore not reliable, the ultrasound signals collected in the M-Mode are relatively robust to noise as compared to other signal types after the ultrasound signals collected in the M-Mode have been treated for noise. For example, a suitable algorithm can be implemented to identify noise signatures in the ultrasound signals collected in the M-Mode and ignore the identified noise signatures in the ultrasound signals collected in the M-Mode. As discussed in further details herein, in some arrangements, the M-Mode energy can be used as the gating or threshold condition in determining the SQA.

In some arrangements, the SQA metric can be defined based on envelope energy. In some examples, an envelope signal is a statistical summary signal determined based on a spectrogram of ultrasound data. The envelope signal can be referred to as a measure of the highest blood velocity values within the insonated vasculature. Generically, the envelope is a value or trace of the maximal spectrogram data range (where the data is non-zero) of the ultrasound data. Fluid dynamics and domain expertise in ultrasound (e.g., TCD) signals indicate that an envelope that models fluid (e.g., blood) flow in vasculature should be smooth. Furthermore, an expected blood flow velocity range can be determined based on information about fluid flow within the vasculature. The envelope energy emphasizes smoothness and velocity range. In one embodiment, the envelope energy minimizes variance in the second derivative of the velocity profile to induce smoothness and penalizes signals of low velocity to encourage high velocity signals. As used herein, penalized refers to lessening of a computed value (e.g., the low-velocity signals). For example, if an original energy value were 100 before considering the velocity range, and the signal has been found to have a low velocity range, the energy value can be penalized by a penalty value (e.g., 30). The final energy (e.g., 70) is the original energy value (e.g., 100) subtracted by the penalty value (e.g., 30). In another embodiment, the envelope energy emphasizes smoothness by minimizing the absolute area between the original signal and the signal processed through a band-pass filter.

Although the envelope energy is more sensitive than the M-Mode energy to noise, the envelope energy is effective in distinguishing good signals from great signals. Given that the envelope energy is more susceptible to noise and typically uses a longer data segment than that of the M-Mode measurements, the envelope energy can be assessed after the M-Mode energy has been determined. As used herein, a data segment (e.g., a span, a signal segment, and so on) refers to a period of data collection time. For example, the envelope energy can be determined responsive to determining that the M-Mode energy exceeds a given threshold.

In some arrangements, the SQA metric can be defined based on BSP energy. The BSP energy corresponds to a spectrogram of the ultrasound data. The spectrogram provides a histogram of blood flow velocities at various velocities. For a given blood flow velocity profile (corresponding to the envelope), the spectrogram shows that some velocity values are near the envelope (or maximum velocity statistic), some velocity values are near zero (zero velocity), and many velocity values are in between the two extremes (e.g., the maximum velocity statistic and the zero velocity).

The BSP energy computes the bounded spectrogram signal power near the value of the envelope. Computed in this way, the BSP constitutes a measure of how much of the velocity histogram is near the peak velocity. The envelope's noise level increases dramatically if the spectrogram power is not concentrated near the envelope. In some examples, this energy function measures the ratio of the spectrogram power bounded near the envelope to the cumulative spectrogram power. In addition, median power of the spectrogram signal over a given data segment also contributes to the BSP energy function. Accordingly, the BSP energy function distinguishes a signal with a strong spectrogram and from a signal with a weak spectrogram.

Therefore, the BSP energy is highly effective in distinguishing a strong signal (e.g., which is the direct result of proper alignment of the ultrasound (e.g., TCD) probe to the vessel of interest). Typically, shorter data segments are used to determine BSP energy. In some arrangements, this BSP energy can be considered in combination with envelope energy and the M-Mode Energy.

In some arrangements, the SQA metric can be defined based on High Frequency Ratio (HFR). Using the frequency domain, HFR is defined as the ratio between the power within a particular frequency band to the power outside of the frequency band. The band is selected based on the expected signal and noise ranges for the underlying data.

In some arrangements, the SQA metric can be defined based on pulsatility index (PI). PI is a parameter that assesses pulsatility of the ultrasound signal. PI is a difference between maximum and minimum blood flow velocity, where the difference is normalized to the average velocity.

In some arrangements, the SQA metric can be defined based on a velocity estimator.

In some arrangements, the SQA metric can be defined based on a parameter that biases the energy towards known vascular locations such that if the probe 105 is pointed at a highly probable area for vasculature, the anatomical energy value would be higher than if the probe 105 were pointed towards low probability areas for signals.

In some arrangements, the SQA metric can be defined to be pathology-specific. For example, for high intracranial pressure for which signals may entirely drop out in the M-Mode and spectrogram (e.g., briefly), SQA metric can be configured to assess such signals.

FIG. 1 is a schematic diagram illustrating a system 100 according to various arrangements. Referring to FIG. 1, the system 100 includes at least a device 110, a controller 130, and an output device 140.

In some examples, the device 110 is an ultrasound device (e.g., a TCD ultrasound device) configured to transmit and/or receive acoustic energy with respect to a head of a subject. The device 110 includes at least one transducer or probe 105 (e.g., at least one ultrasound probe) configured to transmit and/or receive ultrasound acoustic energy with respect to the head. For example, the probe 105 includes at least one TCD transducer. The probe 105 can be configured to collect the ultrasound data in the manner described to find a high-quality signal within a temporal window region (temple) of the head. In other arrangements, the probe can be configured to collect the ultrasound data in the manner described to find a high-quality signal within different acoustic windows such as but not limited to, a temporal window, a transorbital window, a suboccipital window, and so on. In some arrangements, the system 100 includes two devices 110, each device 110 including an ultrasound probe 105, which can be placed near or on the temporal window region on either side of the head (e.g., a first device 110 including a probe 105 at a first side of the head and a second device 110 including a probe 106 at a second side of the head that is opposite to the first side of the head). A lubricating gel can be applied between the head and the probe 105 to improve acoustic transmission.

The controller 130 is configured to receive the ultrasound data collected and output by the device 110 and to perform signal processing for the ultrasound data. In that regard, the device 110 is operatively coupled to the controller 130 via a suitable network 120 to send the ultrasound data to the controller 130. The network 120 can be wired or wireless (e.g., 802.11X, ZigBee, Bluetooth®, Wi-Fi, or the like). The controller 130 is configured to assess signal quality of the ultrasound data in the manner described. In some examples, the controller 130 is further configured to perform signal processing functions such as but not limited to, beat segmentation, morphological feature identification, and so on to facilitate a physician, clinician, technician, or healthcare provider with diagnosis. Further, as described, the device 110 can automatically adjust or reposition the position and orientation of the probe 105 responsive to a determination that the probe 105 is not optimally placed based on the signal quality indicator (e.g., the SQA metric) in the manner described herein. In some arrangements, the controller 130, the output device 140, and a portion of the network 120 are incorporated into a single device (e.g., a touchscreen tablet device).

In some arrangements, the output device 140 includes any suitable device configured to display information, results, messages, and the like to an operator (e.g., a physician, clinician, technician, or care provider) of the system 100. For example, the output device 140 includes but is not limited to, a monitor, a touchscreen, or any other output device configured to display the ultrasound data (e.g., cerebral blood flow velocity (CBFV) waveforms), morphology indicators corresponding to the ultrasound data, and so on for facilitating diagnosis.

In some examples, the signal quality indicator (e.g., the SQA metric) can be used either in real-time signal quality assessment (for real-time decision by, e.g., the device 110 or for morphological analysis) or for post-processing signals quality assessment (e.g., inclusion decision for features into machine learning models). With respect to real-time signal quality assessment, data collected by the device 110 is collected and assessed using the SQA metric in real-time (e.g., as the data is received from the device 110 during a live scan).

With respect to post-processing signals quality assessment, the data collected by the device 110 or another device similar to the device 110 can be stored in a signal database 160 to be processed later. The data (e.g., signal segments) previously stored in the signal database 160 can be subsequently evaluated (e.g., using the SQA metric) for utility in diagnostics, machine learning feature extraction, and so on.

In some arrangements, the system 100 as described herein is used in conjunction with other diagnostic ultrasound procedures, such as, but not limited to, needle guidance, intravascular ultrasound (e.g., examination of vessels, blood flow characteristics, clot identification, emboli monitoring, and so on), echocardiograms, abdominal sonography (e.g., imaging of the pancreas, aorta, inferior vena cava, liver, gall bladder, bile ducts, kidneys, spleen, appendix, rectal area, and so on), gynecologic ultrasonography (e.g., examination of pelvic organs such as uterus, ovaries, Fallopian tubes, and so on), obstetrical sonography, otolaryngological sonography (e.g., imaging of the thyroid (such as for tumors and lesions), lymph nodes, salivary glands, and so on), neonatal sonography (e.g., assessment of intracerebral structural abnormalities through soft spots of a skull of an infant, bleeds, ventriculomegaly, hyrdrocephalus, anoxic insults, and so on), ophthamological procedures (e.g., A-scan ultrasound biometry, B-scan ultrasonography, and so on), pulmonological uses (e.g., endobronchial ultrasound (EBUS)), urological procedures (e.g., determination of an amount of fluid retained in a subject's bladder, imaging of pelvic organs (such as uterus, ovaries, urinary bladder, prostate, and testicles), and detection of kidney stones), scrotal sonography (e.g., to evaluate testicular pain, identify solid masses, and so on), musculoskeletal procedures (e.g., examination of tendons, muscles, nerves, ligaments, soft tissue masses, bone surfaces, and so on), bone fracture sonography, testing for myopathic disease, estimating lean body mass, proxy measures of muscle quality (e.g., tissue composition), nephrological procedures (e.g., renal ultrasonography), and the like.

In some arrangements, the system 100 as described herein is used in conjunction with therapeutic ultrasound procedures, such as, but not limited to, high-intensity focused ultrasound (HIFU), focused ultrasound surgery (FUS), Magnetic resonance-guided focused ultrasound (MRgFUS), lithotripsy (e.g., breaking up kidney stones, bezoars, gall stones, and the like), targeted ultrasound drug delivery, trans-dermal ultrasound drug delivery, ultrasound hemostasis, cancer therapy, ultrasound-assisted thrombolysis, dental hygiene (e.g., cleaning teeth), phacoemulsification, ablation (e.g., of tumors or other tissue), acoustic targeted drug delivery (ATDD), trigger release of drugs (e.g., anti-cancer drugs), ultrasound-guided treatments (sclerotherapy, endovenous laser treatment, liposuction, and so on), and the like. In some arrangements, ultrasound is used for physical therapy applications, including, but not limited to, stimulating tissue beneath the skin's surface (e.g., by using very high frequency sound waves, such as, as an example, between about 800,000 Hz and 2,000,000 Hz), treating musculoskeletal ailments with ultrasound exposure (e.g., ligament sprains, muscle strains, tendonitis, joint inflammation, plantar fasciitis, metatarsalgia, facet irritation, impingement syndrome, bursitis, rheumatoid arthritis, osteoarthritis, and scar tissue adhesion), and the like.

Figure 2:
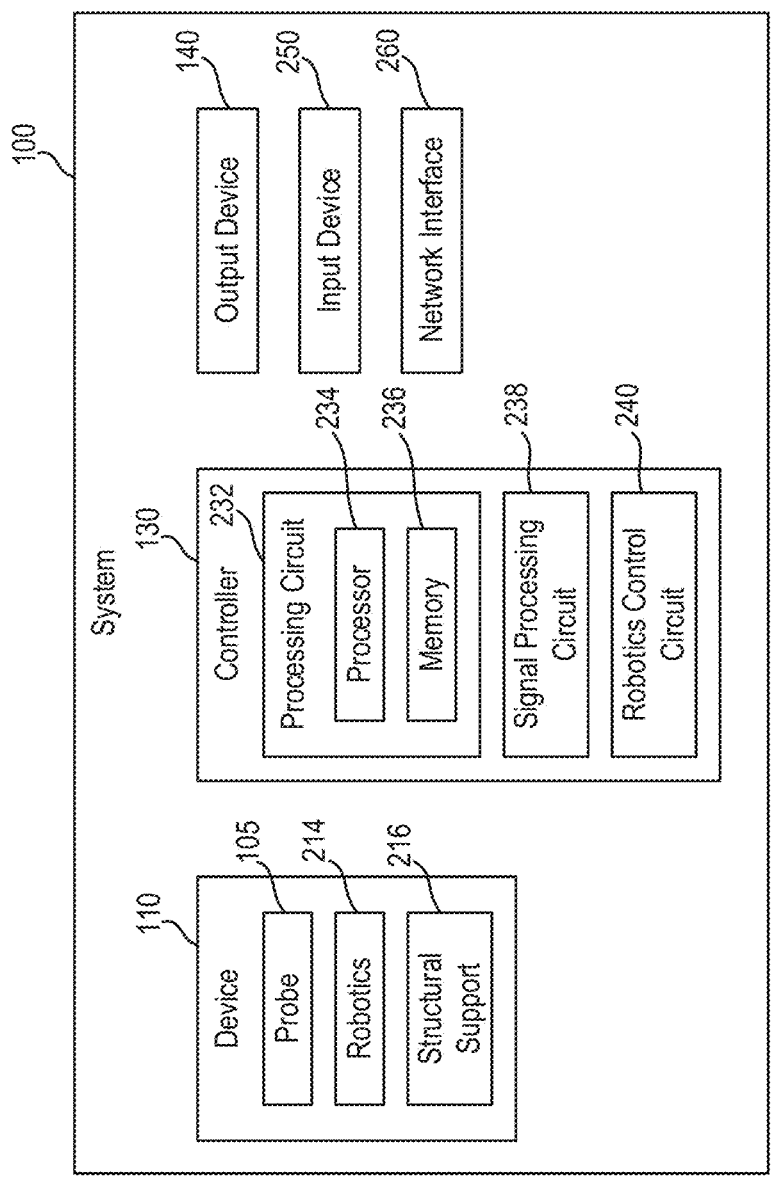
FIG. 2 is a schematic block diagram illustrating the system (FIG. 1) according to various arrangements.

FIG. 2 is a schematic block diagram illustrating the system 100 (FIG. 1) according to various arrangements. Referring to FIGS. 1-2, the device 110 includes the probe 105 as described. Further disclosure regarding examples of the probe 105 that can be used in conjunction with the system 100 described herein can be found in non-provisional patent Publication no. US 2017/0119347, titled ROBOTIC SYSTEMS FOR CONTROL OF AN ULTRASONIC PROBE, and filed on Jan. 5, 2017, which is incorporated herein by reference in its entirety. In some arrangements, the device 110 is configured to automatically or robotically operate the probe 105.

In some arrangements, the device 110 includes robotics 214 configured to control positioning of the probe 105. For example, the robotics 214 are configured to translate the probe 105 along a surface of the head and to move the probe 105 with respect to (e.g., toward and away from) the head along various axes in the Cartesian, spherical, and rotational coordinate systems. In particular, the robotics 214 can include a multiple degree of freedom (DOF) TCD transducer positioning system with motion planning. In some arrangements, the robotics 214 are capable of supporting two, three, four, five, or six DOF movements of the probe 105 with respect to the head. In some instances, the robotics 214 can translate in X and Y axes (e.g., along a surface of the head) to locate a temporal window region in translational axes, and in Z axis with both force and position feedback control to both position, and maintain the appropriate force against the skull/skin to maximize signal quality by maintaining appropriate contact force. Two angular DOF (e.g., pan and tilt) may be used to maximize normal insonation of blood vessels to maximize velocity signals.

In some arrangements, an end of the probe 105 is operatively coupled to or otherwise interfaces with the robotics 214. The robotics 214 include components, such as but not limited to a motor assembly and the like for controlling the positioning of the probe 105 (e.g., controlling z-axis pressure, normal alignment, or the like of the probe 105). In some arrangements, the registration of the probe 105 against the head 105 is accomplished using the robotics 214 to properly position and align the probe 105 in the manner described.

In some arrangements, the probe 105 includes a first end and a second end that is opposite to the first end. In some arrangements, the first end includes a concave surface that is configured to be adjacent to or contact a scanning surface on the head. The concave surface is configured with a particular pitch to focus generated energy towards the scanning surface. In some arrangements, the device 110 is a TCD apparatus such that the first end of the probe 105 is configured to be adjacent to or contact and align along a side of the head. The first end of the probe 105 is configured to provide ultrasound wave emissions from the first end and directed into the head (e.g., toward the brain). For example, the first end of the probe 105 can include a transducer (such as, but not limited to, an ultrasound transducer, TCD, transcranial color-coded sonography (TCCS), or acoustic ultrasound transducer array such as sequential arrays or phased arrays) that emits acoustic energy capable of penetrating windows in the skull/head or neck.

In some arrangements, the second end of the probe 105 is coupled to the robotics 214. In some arrangements, the second end of the probe 105 includes a threaded section along a portion of the body of the probe 105. The second end is configured to be secured in the robotics 214 via the threads (e.g., by being screwed into the robotics 214). In other arrangements, the probe 105 is secured in the robotics 214 by any other suitable connecting means, such as but not limited to welding, adhesive, one or more hooks and latches, one or more separate screws, press fittings, or the like.

In other arrangements, the device 110 does not include robotics 214 and the probe 105 is manually operated and moved by a technician.

The device 110 can further include a structural support 216 configured to support the head of the subject and/or to support the device 110 on the head or other parts of a body of the subject. In some examples, the structural support 216 includes a platform (e.g., a baseplate) that allows the subject to lay down on a flat surface in a reclined or supine position while the device 110 is operational. The structural support 216 can be made from any suitably malleable material that allows for flexing, such as, but not limited to, flexible plastics, polyethylene, urethanes, polypropylene, ABS, nylon, fiber-reinforced silicones, structural foams, or the like.

In some arrangements, the system 100 includes an input device 250. The input device 250 includes any suitable device configured to allow an operator, physician, or care provider personnel to input information or commands into the system 100. In some arrangements, the input device 250 includes but is not limited to, a keyboard, a keypad, a mouse, a joystick, a touchscreen display, a microphone, or any other input device performing a similar function. In some arrangements, the input device 250 and the output device 140 can be a same input/output device (e.g., a touchscreen display device).

In some arrangements, the network interface 260 is structured for sending and receiving data (e.g., results, instructions, requests, software or firmware updates, and the like) over a communication network (e.g., the network 120). Accordingly, the network interface 260 includes any of a cellular transceiver (for cellular standards), local wireless network transceiver (for 802.11X, ZigBee, Bluetooth®, Wi-Fi, or the like), wired network interface, a combination thereof (e.g., both a cellular transceiver and a Bluetooth transceiver), and/or the like. In some examples, the network interface 260 includes any method or device configured to send data from the device 110 to the controller 130. In that regard, the network interface 260 may include Universal Serial Bus (USB), FireWire, serial communication, and the like.

In some arrangements, the input device 250, the output device 140, the network interface 260, and the controller 130 form a single computing system that resides on a same node on the network 120. The device 110 is configured to be connected to the computing system via the network 120. The network interface 260 is configured to communicate data to and from the device 110 via the network 120. In such arrangements, the device 110 includes a similar network interface (not shown) to communicate data to and from the computing device via the network 120. In other arrangements in which the device 110, the controller 130, the output device 140, the input device 250, and the network interface 260 all reside in a same computing device on a same node of a network, the network interface 260 is configured to communicate data with another suitable computing system (e.g., cloud data storage, remote server, and the like).

In some arrangements, the controller 130 is configured for controlling operations, processing data, executing input commands, providing results, and so on. For example, the controller 130 is configured to receive input data or instructions from the input device 250 or the network interface 260, to control the system 100 to execute the commands, to receive data from the device 110, to provide information to the output device 140 or network interface 260, and so on.

The controller 130 includes a processing circuit 232 having a processor 234 and a memory 236. In some arrangements, the processor 234 can be implemented as a general-purpose processor and is coupled to the memory 236. The processor 234 includes any suitable data processing device, such as a microprocessor. In the alternative, the processor 234 includes any suitable electronic processor, controller, microcontroller, or state machine. In some arrangements, the processor 234 is implemented as a combination of computing devices (e.g., a combination of a Digital Signal Processor (DSP) and a microprocessor, a plurality of microprocessors, at least one microprocessor in conjunction with a DSP core, or any other such configuration). In some arrangements, the processor 234 is implemented as an Application Specific Integrated Circuit (ASIC), one or more Field Programmable Gate Arrays (FPGAs), a Digital Signal Processor (DSP), a group of processing components, or other suitable electronic processing components.

In some arrangements, the memory 236 includes a non-transitory processor-readable storage medium that stores processor-executable instructions. In some arrangements, the memory 236 includes any suitable internal or external device for storing software and data. Examples of the memory 236 include but are not limited to, Random Access Memory (RAM), Read-Only Memory (ROM), Non-Volatile RAM (NVRAM), flash memory, floppy disks, hard disks, dongles or other Recomp Sensor Board (RSB)-connected memory devices, or the like. The memory 236 can store an Operating System (OS), user application software, and/or executable instructions. The memory 236 can also store application data, such as an array data structure. In some arrangements, the memory 236 stores data and/or computer code for facilitating the various processes described herein.

As used herein, the term "circuit" can include hardware structured to execute the functions described herein. In some arrangements, each respective circuit can include machine-readable media for configuring the hardware to execute the functions described herein. The circuit can be embodied as one or more circuitry components including, but not limited to, processing circuitry, network interfaces, peripheral devices, input devices, output devices, sensors, etc. In some arrangements, a circuit can take the form of one or more analog circuits, electronic circuits (e.g., integrated circuits (IC), discrete circuits, system on a chip (SOCs) circuits, etc.), telecommunication circuits, hybrid circuits, and any other suitable type of circuit. In this regard, the circuit can include any type of component for accomplishing or facilitating achievement of the operations described herein. For example, a circuit as described herein can include one or more transistors, logic gates (e.g., NAND, AND, NOR, OR, XOR, NOT, XNOR, etc.), resistors, multiplexers, registers, capacitors, inductors, diodes, wiring, and so on.

The circuit can also include one or more processors communicatively coupled to one or more memory or memory devices. In this regard, the one or more processors can execute instructions stored in the memory or can execute instructions otherwise accessible to the one or more processors. In some arrangements, the one or more processors can be embodied in various ways. The one or more processors can be constructed in a manner sufficient to perform at least the operations described herein. In some arrangements, the one or more processors can be shared by multiple circuits (e.g., a first circuit and a second circuit can comprise or otherwise share the same processor which, in some example arrangements, can execute instructions stored, or otherwise accessed, via different areas of memory). Alternatively, or additionally, the one or more processors can be structured to perform or otherwise execute certain operations independent of one or more co-processors. In other example arrangements, two or more processors can be coupled via a bus to enable independent, parallel, pipelined, or multi-threaded instruction execution. Each processor can be implemented as one or more general-purpose processors, ASICs, FPGAs, DSPs, or other suitable electronic data processing components structured to execute instructions provided by memory. The one or more processors can take the form of a single core processor, multi-core processor (e.g., a dual core processor, triple core processor, quad core processor, etc.), microprocessor, etc. In some arrangements, the one or more processors can be external to the apparatus, for example, the one or more processors can be a remote processor (e.g., a cloud-based processor). Alternatively, or additionally, the one or more processors can be internal and/or local to the apparatus. In this regard, a given circuit or components thereof can be disposed locally (e.g., as part of a local server, a local computing system, etc.) or remotely (e.g., as part of a remote server such as a cloud-based server). To that end, a circuit, as described herein can include components that are distributed across one or more locations.

An example system for implementing the overall system or portions of the arrangements can include a general-purpose computer, including a processing unit, a system memory, and a system bus that couples various system components including the system memory to the processing unit. Each memory device can include non-transient volatile storage media, non-volatile storage media, non-transitory storage media (e.g., one or more volatile and/or non-volatile memories), etc. In some arrangements, the non-volatile media may take the form of ROM, flash memory (e.g., flash memory such as NAND, 3D NAND, NOR, 3D NOR, etc.), Electrically Erasable Programmable Read-Only Memory (EEPROM), Magnetoresistive Random Access Memory (MRAM), magnetic storage, hard discs, optical discs, etc. In other arrangements, the volatile storage media can take the form of RAM, Thyristor Random Access Memory (TRAM), Z-Capacitor Random Access Memory (ZRAM), etc. Combinations of the above are also included within the scope of machine-readable media. In this regard, machine-executable instructions comprise, for example, instructions and data which cause a general-purpose computer, special purpose computer, or special purpose processing machines to perform a certain function or group of functions. Each respective memory device can be operable to maintain or otherwise store information relating to the operations performed by one or more associated circuits, including processor instructions and related data (e.g., database components, object code components, script components, etc.), in accordance with the example arrangements described herein.

The controller 130 further includes a signal processing circuit 238, which can be implemented with the processing circuit 232 or another dedicated processing circuit. In some examples, the signal processing circuit 238 can be implemented with two or more circuits. The signal processing circuit 238 receives the ultrasound data from the device 110 and assesses signal quality of the ultrasound data by determining the SQA metric and comparing the SQA metric against a threshold. In some arrangements the threshold is determined by the demography of the patient. In some arrangements the threshold is dynamically adjusted as more data is collected. This allows for the SQA thresholds to be flexibly deployed in new scenarios wherein the specific signal quality differs drastically from that of the normative population.

In some arrangements, different signals (e.g., signals collected from different locations on a same object, or signals collected from the same location of the same object but at different times, and so on) can be graded based on the SQA metric for each of the different signals. That is, the SQA values are compared between different signal points. For example, point A and point B correspond to SQA values of 90 and 100 respectively. Both of the SQA values may be over a threshold of 80 (if a threshold is implemented), so that both of the SQA values may be considered to be "high quality." In some cases, the ultrasound data for point B may be selected for processing given that point B has a better signal as the SQA value is 100.

In some arrangements, responsive to determining that the ultrasound data has signal quality above a threshold or determining that the ultrasound data has the highest signal quality among multiple points, the signal processing circuit 238 is configured to generate the CBFV waveforms by performing beat segmentation, determine the morphology indicators for the CBFV waveforms, and so on. The signal processing circuit 238 can configure the output device 140 to display the CBFV waveforms, the morphology indicators, and other relevant health information. In some examples, responsive to determining that the ultrasound data has signal quality above a threshold or determining that the ultrasound data has the highest signal quality among multiple points, a next search phase in an automated signal search process can be executed. In some examples, each search phase in the automated signal search corresponds to a given location on the subject, a given step in the workspace, a given signal collection mode, and so on. Each phase typically has a corresponding SQA threshold to be achieved before moving to the next phase.

The controller 130 further includes a robotic control circuit 240, which can be implemented with the processing circuit 232 or another dedicated processing circuit. The robotic control circuit 240 is configured to control the robotics 214 to move the probe 105 in the manner described.

In the post-processing scenario, signal segments of the ultrasound data stored in the signal database 160 is assessed using the SQA metric for utility in diagnostics, machine learning feature extraction, and so on. For example, responsive to determining that the SQA metric for the ultrasound data is above the threshold as described herein, the ultrasound data is admissible to be used as a part of a training data set or testing data set for machine learning algorithms, for testing and training improved diagnostic settings, for determining improved search algorithms, and so on. On the other hand, responsive to determining that the SQA metric for the ultrasound data is not above the threshold as described herein, the ultrasound data is disregarded or discarded.

Figure 3:
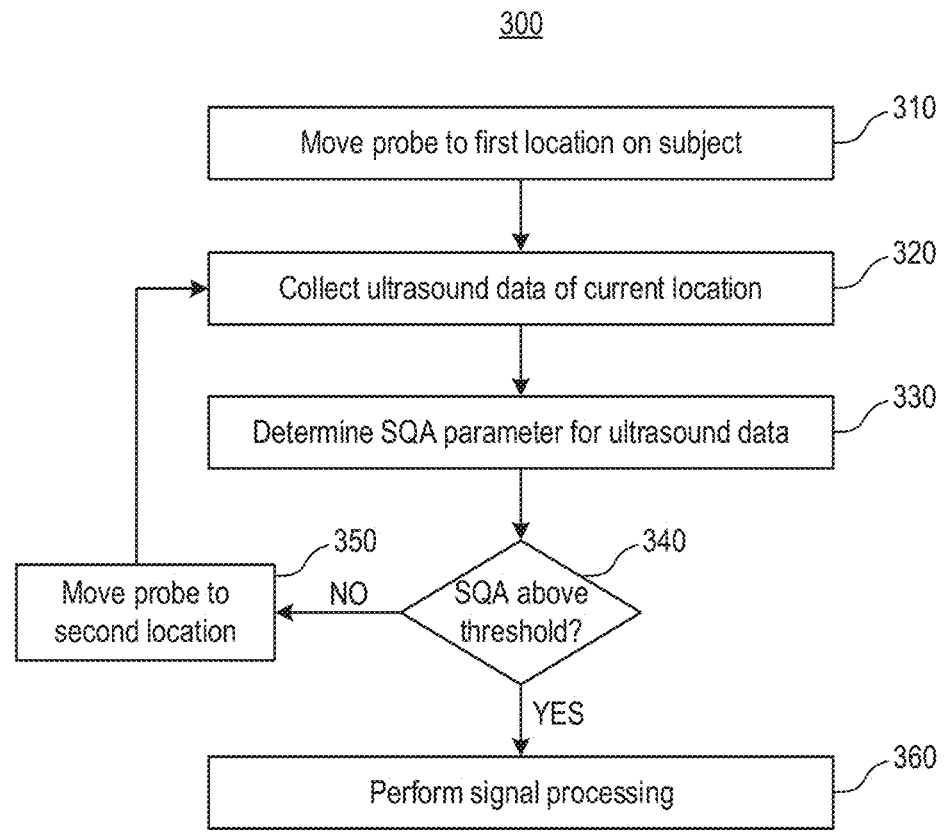
FIG. 3 is a process flow diagram illustrating a method for assessing signal quality using the system (FIG. 1) according to various arrangements.

FIG. 3 is a process flow diagram illustrating a method 300 for assessing signal quality using the system 100 (FIG. 1) according to various arrangements. Referring to FIGS. 1-3, blocks 310-350 correspond to a search process in which the probe 105 is moved by the robotics 214 (e.g., at blocks 310 and 350) to various different locations on the subject to identify locations on the subject that yield a high quality signal. Once a high quality signal is identified at a certain location, the probe 105 can then be configured to collect ultrasound data in the location identified as having high signal quality. The signal processing circuit 238 can then perform signal processing (e.g., at block 360) on such high-quality signals, for example, to generate useful information (e.g., morphology indicators).

Figure 4:
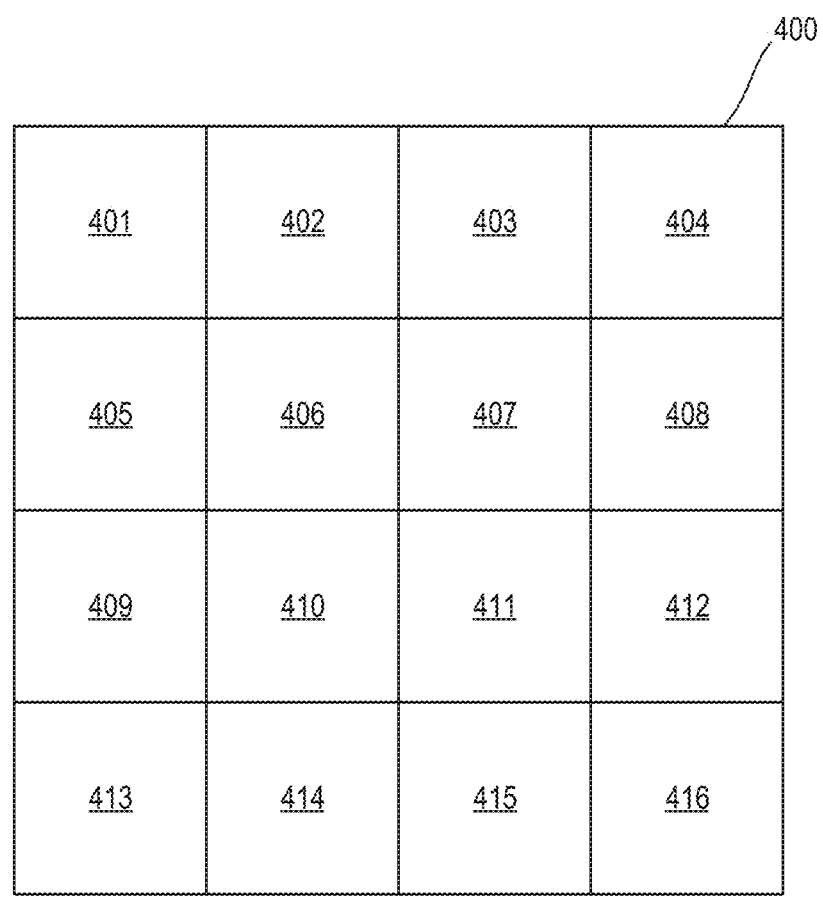
FIG. 4 is a schematic diagram illustrating areas of an example workspace according to various arrangements.

At 310, the robotics 214 are configured by the robotics control circuit 240 to move the probe 105 to a first location on a subject. The probe 105 may be controlled to move within a workspace. FIG. 4 is a schematic diagram illustrating areas 401-416 of an example workspace 400 according to various arrangements. Referring to FIGS. 1-4, the workspace 400 of the probe 105 may correspond to a maximum allowable boundary which the robotics 214 can move the probe 105. While shown to be planar (e.g., in an XY-plane), the workspace 400 can be 3-dimensional (in an XYZ-space). While the workspace 400 and the areas 401-416 are shown to be squares, the workspace 400 and the areas 401-416 can have any suitable shape such as but not limited to, triangles, rectangles, circles, pentagons, hexagons, irregular shapes, and so on. In some examples, each of the areas 401-416 corresponds to a discrete step or location by which the probe 105 is configured to move. The probe 105 can be moved from a center of one of the areas 401-416 to a center of an adjacent one of the areas 401-416. The center of each of the areas 401-416 corresponds to a location. The probe 105 may not stop between the centers of two adjacent ones of the areas 401-416 to collect any ultrasound data. As an example, the robotics 214 are configured by the robotics control circuit 240 to move the probe 105 from the center of the area 401 (the first location), then to the center of the area 402 (a second location), then to the center of the area 403 (a third location), then to the center of the area 404 (a fifth location), then to the center of the area 408 (a sixth location), and so on. In other arrangements, instead of the moving in discrete steps within the workspace 400, the probe 105 may be configured to move continuously within the workspace 400 as the ultrasound data is computed.

The probe 105 may have various different orientations at each position. Thus, different signals can be collected for different orientations of the probe 105 at a given position, where a SQA metric can also be computed for each of the different orientations. In other arrangements, instead of the probe 105 moving in discrete steps, the probe 105 may be moved to traverse within the boundaries of the workspace 400 continuously.

Figure 5:
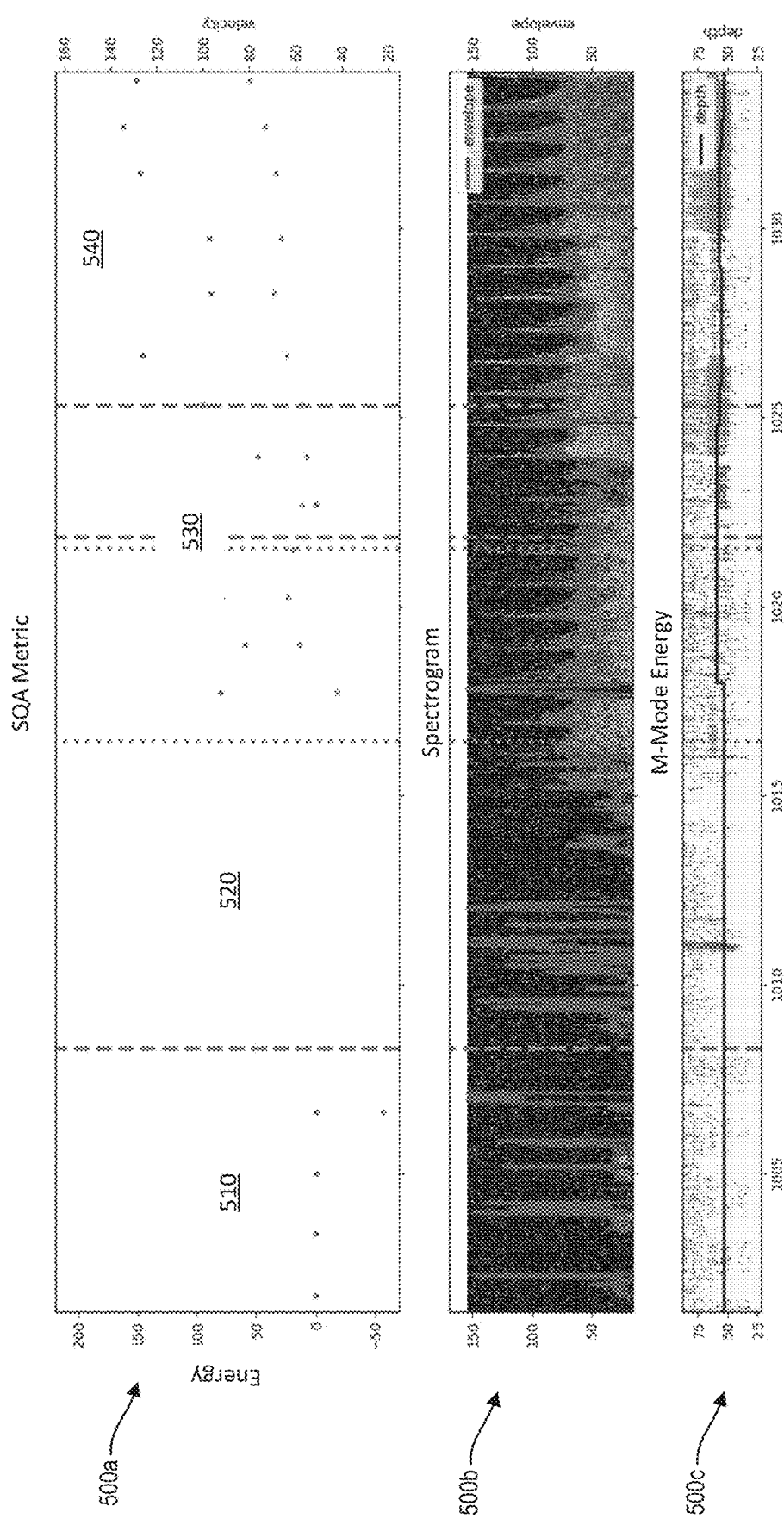
FIG. 5 illustrates graphs of a SQA metric of a signal, a spectrogram of the signal, and M-Mode energy of the signal according to various arrangements.

At 320, the probe 105 is configured to receive ultrasound data of a current location (e.g., the first location, which is the center of the area 401) of the probe 105. At 330, the signal processing circuit 238 of the controller 130 is configured to determine an SQA metric for the ultrasound data. FIG. 5 illustrates a graph 500a of an SQA metric of a signal according to various arrangements. In some examples, the SQA metric for the ultrasound data is determined based on at least one energy function of the ultrasound data.

An example energy function is the M-Mode energy. FIG. 5 illustrates a graph 500c of a M-Mode energy of a signal according to various arrangements. To determine the M-Mode energy, the probe 105 is configured by the signal processing circuit 238 to collect the ultrasound data (e.g., at block 320) in an M-Mode. The M-Mode energy is determined using the ultrasound data collected in the M-Mode as described.

Another example energy function is the envelope energy. To determine the envelope energy, the probe 105 is configured by the signal processing circuit 238 to collect the ultrasound data (e.g., at block 320). The signal processing circuit 238 is configured to determine a spectrogram of the ultrasound data and determine the envelope energy using the spectrogram. FIG. 5 illustrates a graph 500b of a spectrogram and envelope of a signal according to various arrangements. In other words, the envelope energy is computed using the envelope, and the envelope is a derived statistic from the spectrogram.

In some examples, the envelope energy includes a velocity estimator and smoothness estimator. The velocity estimator and the smoothness estimator are two components of the envelope energy. The signal processing circuit 238 determines the velocity estimator by determining a median of a predetermined data segment (e.g., the last 2 seconds) of the envelope of the ultrasound signal. In other examples, median velocity values over a set of movements of the probe 105 convolved with a half-Gaussian may be used for the velocity estimator. The signal processing circuit 238 determines the smoothness estimator by filtering the ultrasound signal using a band-pass filter to obtain a smoothed ultrasound signal. The signal processing circuit 238 then determines the smoothness estimator for the smoothed ultrasound signal. The smoothness estimator computes the absolute difference (area between the curves) between the smoothed (band-passed) velocity curves. The smaller the smoothness estimator is, the smoother the original signal is.

Another example energy function is the BSP energy. To determine the BSP energy, the probe 105 is configured by the signal processing circuit 238 to collect the ultrasound data (e.g., at block 320). The signal processing circuit 238 is configured to determine a spectrogram of the ultrasound data and determine the BSP energy using the spectrogram. FIG. 5 illustrates a graph 500*b* of a spectrogram and envelope of a signal according to various arrangements.

Another example energy function is the HFR. To determine the HFR, the probe 105 is configured by the signal processing circuit 238 to collect the ultrasound data (e.g., at block 320). The signal processing circuit 238 is configured to determine an envelope and determine the HFR using the envelope (such as but not limited to, that which is shown in the graph 500*b*).

Another example energy function is the PI. The signal processing circuit 238 is configured to determine a difference between maximum and minimum blood flow velocity, and normalize the difference to the average velocity.

In some examples, the ultrasound data used to determine each of the energy functions described herein is collected all at once, and energy functions are computed from the collected data after all the ultrasound data has been collected. The energy functions are then combined into the SQA metric (e.g., a single value or utilized as an energy vector) as described herein.

In other examples, given that the energy functions described herein may be determined based on ultrasound data measured in different modalities, block 320 can be iteratively executed for each energy function needed to determine the SQA metric. For example, given that a relative shorter data segment (shorter than the data segments of other energy functions) is needed for collecting the ultrasound data in the M-Mode, and that the M-Mode energy can be used as a gating/threshold energy function, collecting the ultrasound data in the M-Mode (at block 320) and determining the M-Mode energy can be executed first, before collecting ultrasound data used to determine other energy functions (e.g., the envelope energy, the BSP energy, the HFR, PI, and so on). In some arrangements, all the energy functions are computed on the same ultrasound data. In some examples, the M-Mode energy is computed first, and the other energy functions are computed in response to determining that the M-Mode energy achieves a certain threshold.

In some arrangements, a combination of the energy functions described herein is used to determine the SQA. In some examples, the input device 250 can be configured to receive user input corresponding to one or more conditions (e.g., emboli, vasospasm, sickle cell, brain death, high intracranial pressure, mild traumatic brain injury (concussion), interoperative monitoring (operating room), patent foramen ovale (PFO), stroke, cryptogenic stroke, and so on) for which ultrasound data is to be collected for diagnosis aid or automatic diagnosis. Each condition may correspond to a subset of all the energy functions described herein. Therefore, depending on the user-selected condition(s), the signal processing circuit 238 can select or weight one or more of the energy functions M-Mode energy, envelope energy, BSP, HFR, PI, and so on corresponding to the condition(s). For example, in response to determining that emboli condition is selected, the M-Mode energy may be selected from all the energy functions described herein, given that M-Mode energy may be needed to assess the ultrasound data signal quality with respect to emboli.

In that regard, for example, the SQA at block 340 can be determined using the following expression:

$$SQA = G(\{F_i\}) \Sigma \alpha_i F_i \quad (1);$$

where $G(\{F_i\})$ is the gating/threshold function, and $\Sigma \alpha_i F_i$ is the sum of all weighted energy functions described herein.

In some examples, $G(\{F_i\})$ is mapped to a set of results $\{0, 1\}$, such that when $G(\{F_i\})=0$, the SQA becomes 0, the signal quality is so poor that additional data collection in other modalities is not needed. On the other hand, when $G(\{F_i\})=1$, the SQA becomes $\Sigma \alpha_i F_i$. In some arrangements, the M-Mode energy can be used as $G(\{F_i\})$ or as a proxy thereof (e.g., $G(\{F_i\})=1$ responsive to determining that M-Mode energy is greater than a M-Mode energy threshold) given that the M-Mode energy is the quickest to compute out of all the energy functions, and that M-Mode energy typically is a sufficient indicator of whether there is any meaningful signal at all (as supposed to only noise). In other arrangements, the ultrasound signals themselves can be analyzed to determine $G(\{F_i\})$.

In some arrangements, $G(\{F_i\})$ can be used to assess whether the probe 105 is at a position that is over a temporal window of the subject. In one example, three states can be assigned for G: G=0 indicates that the probe 105 is not over a temporal window; G=0.5 indicates that the probe 105 is over a temporal window but no signal is collected by the probe 105; and G=1 indicates that the probe 105 is collecting M-mode signal of sufficient quality to consider determining the SQA metric (e.g., by computing the SQA metric). To assess whether the probe 105 is over a temporal window using $G(\{F_i\})$, $G(\{F_i\})$ may be determined based on an energy component (e.g., as a function of one or more of the spectrogram, the M-Mode, and so on) that indicates whether or not the probe 105 is over a temporal window.

The scalar $\alpha_i$ can be determined based on the user input (e.g., the selected condition(s)). The scalar $\alpha_i$ being set to 0 means that the energy function $F_i$ is not considered for the selected condition(s). The scalar $\alpha_i$ being set to 1 means that the energy function $F_i$ is considered at its full value for the selected condition(s). The scalar $\alpha_i$ being set to be greater than 1 means that the energy function $F_i$ is weighted higher than other components. The scalar $\alpha_i$ being set to be less than 0 means that the energy function $F_i$ is penalized.

At 340, the signal processing circuit 238 determines whether the SQA metric is above a threshold. The threshold may be dynamic in some examples. That is, the threshold may start from an initial value, where the threshold increases from the initial value if the initial value is exceeded, for example, continuously, semi-continuously, a certain number of instances, at least once, and so on for a period of time (e.g., 2 seconds, 5 seconds, 10 seconds, and so on) and decreases from the initial value if the initial value is not exceeded continuously, semi-continuously, a certain number of instances, at least one, and so on for the period of time. The new threshold value then becomes the initial value, and thus making the threshold dynamic. In an example in which the initial value of the threshold is 100, responsive to determining that the initial value is met, the threshold may increase by a predetermined percentage (e.g., 15%, to 115). The threshold can decay over time if the new threshold (e.g., 115) has not been exceeded, e.g., eventually the threshold decays to 110. Responsive to determining that the SQA metric exceeds the threshold at 110, then the threshold may be increased by 15% to 126.5, and so on.

Responsive to determining that the SQA is not above the threshold (340: NO), the robotics 214 may be configured to move the probe 105 to a second location at 350. The probe 105 is configured to collect the ultrasound data of the current location (e.g., the second location) at 320, for determining another SQA at 330. That is, the probe 105 can be configured to collect ultrasound data to access signal quality in an adjacent location (e.g., the area 402) adjacent to the first location (e.g., the area 401) or in another location (e.g., the area 403) not adjacent to the first location.

Responsive to determining that the SQA is above the threshold (340: YES), the signal processing circuit 238 may perform signal processing at 360. Signal processing may include beat segmentation, identifying morphology features, and so on. The output device 140 can be configured to display the morphology features. In some examples, responsive to determining that the SQA is above the threshold (340: YES), a next search phase of multiple search phases of the search may be triggered. If the current search phase is the final search phase of the multiple search phases, the position at which the probe 105 is may be saved for revisiting on the subject (e.g. for monitoring of the signal for any TCD examination) and/or the probe 105 may remain in the position. For a cached/saved position, the processing circuit 232 may leverage signal processing of the ultrasound data for diagnostics (e.g. for emboli, vasospasm, and so on). The ultrasound data can additionally be uploaded via the network 120 to the cloud (not shown) for further processing (e.g. for diagnostics, remote visualization, and so on). In some examples, the SQA method described herein allows an operator to see high-quality ultrasound data and perform any procedures-based diagnostics from what the operator sees in the recorded signals. In some examples, for example in offline systems utilizing the database 160, 340: YES would allow a signal to be admitted for use, for example, with respect to machine learning algorithms for training or testing in different diagnostic settings or for improving search algorithms.

In the examples in which the probe 105 is continuously moved within the workspace 400, the SQA assessment may be executed in parallel with moving the probe 105. The continuous SQA assessment can be used to continually update the continuous movement trajectory path of the probe 105. A given trajectory path may include at least one of one or more straight lines, one or more curved lines, and so on. In one example, the trajectory path may be a serpentine path within the workspace 400 of the probe 105. The trajectory path may be predefined, and the robotics 214 are configured to move the probe 105 along a given trajectory path continuously (without stopping until the trajectory path is completed). In some arrangements, a trajectory path can be changed in the middle of moving the probe 105 along that trajectory path based on the SQA metric. In one example, responsive to determining that the SQA metric with respect to a first location on a first trajectory path is not above the threshold (similar to 340: NO), the robotics 214 may be configured to move the probe 105 to change the current path from the first trajectory path to a second trajectory path different from the first trajectory path. For instance, the robotics 214 may be configured to move the probe 105 to a second location on the second trajectory path, where the second location may not be on the first trajectory path. In other words, responsive to determining that the first location on the first trajectory path has low signal quality, the trajectory path may be changed. In another example, responsive to determining that the SQA metric of a segment (e.g., a continuous portion) of the first trajectory path is deteriorating (e.g., having progressively lower signal quality in the segment), the robotics 214 may be configured to move the probe 105 to change the current path from the first trajectory path to a second trajectory path different from the first trajectory path. For instance, the robotics 214 may be configured to move the probe 105 to a second location on the second trajectory path, where the second location may not be on the first trajectory path. The segment may have a predefined length (e.g., 1 mm, 2 mm, 5 mm, 10 mm, and so on). The SQA metric for the segment is deteriorating in response to determining that any prior location on the segment has a SQA metric indicative of higher signal quality than a SQA metric of any subsequent location on the segment.

FIG. 5 shows the graph 500b of the spectrogram and the graph 500c of the M-Mode energy of an ultrasound signal, and the graph 500a of the determined SQA metric of that continuous ultrasound signal, in some arrangements. As shown, the signal quality of the ultrasound signal can be quantified using one or more aspects of the spectrogram (e.g., the envelope) and the M-Mode energy, which affect and correlate with the SQA metric. For example, as shown, during a first data segment 510, the signal quality is low (e.g., the ultrasound signal is almost nonexistent) as shown in the graphs 500b and 500c. This is reflected in a low (e.g., zero or sub-zero) SQA metric in the graph 500a. During a second data segment 520, there is no SQA metric output because the device 110 (e.g., the probe 105) is not collecting ultrasound signals during the second data segment 520. In one example, the probe 105 may be moved by the robotics 214 during the second data segment 520, and the probe 105 is not collecting ultrasound signals during the move (e.g., the probe 105 is being configured to move in discrete steps as described). During a third data segment 530, an ultrasound signal of relatively decent quality is found, as shown in the graphs 500b and 500c. Correspondingly, the SQA metric during the third data segment 530 improves (e.g., having higher values as compared to those determined during the first data segment 510). During a fourth data segment 540, an ultrasound signal of higher quality than that found in the third data segment 530 is found, as shown in the graphs 500b and 500c. Correspondingly, the SQA metric during the fourth data segment 540 has higher values as compared to those determined during the first data segment 510 and the third data segment 530.

In some arrangements, graph 500a is displayed on an output device of the system 100 (e.g., at the output device 140). One or more of the graphs 500b and 500c may also be displayed. In other arrangements, the SQA metric is displayed in different suitable ways other than as shown in the graph 500a, such as, but not limited to, a percentage or other value from 0 to 100 indicating the lowest SQA metric value to the highest SQA metric value, respectively, a dial indicating the value of the SQA metric, a meter, and so on. In some arrangements, this visualization at a display indicating a current SQA metric can be updated in real time as the robotic or manual probe 105 is operated at the subject.

The above used terms, including "held fast," "mount," "attached," "coupled," "affixed," "connected," "secured," and the like are used interchangeably. In addition, while certain arrangements have been described to include a first element as being "coupled" (or "attached," "connected," "fastened," etc.) to a second element, the first element may be directly coupled to the second element or may be indirectly coupled to the second element via a third element.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout the previous description that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

It is understood that the specific order or hierarchy of steps in the processes disclosed is an example of illustrative approaches. Based upon design preferences, it is understood that the specific order or hierarchy of steps in the processes may be rearranged while remaining within the scope of the previous description. The accompanying method claims present elements of the various steps in a sample order, and are not meant to be limited to the specific order or hierarchy presented.

The previous description of the disclosed implementations is provided to enable any person skilled in the art to make or use the disclosed subject matter. Various modifications to these implementations will be readily apparent to those skilled in the art, and the generic principles defined herein may be applied to other implementations without departing from the spirit or scope of the previous description. Thus, the previous description is not intended to be limited to the implementations shown herein but is to be accorded the widest scope consistent with the principles and novel features disclosed herein.

The various examples illustrated and described are provided merely as examples to illustrate various features of the claims. However, features shown and described with respect to any given example are not necessarily limited to the associated example and may be used or combined with other examples that are shown and described. Further, the claims are not intended to be limited by any one example.

The foregoing method descriptions and the process flow diagrams are provided merely as illustrative examples and are not intended to require or imply that the steps of various examples must be performed in the order presented. As will be appreciated by one of skill in the art the order of steps in the foregoing examples may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the examples disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The preceding description of the disclosed examples is provided to enable any person skilled in the art to make or use the present disclosure. Various modifications to these examples will be readily apparent to those skilled in the art, and the generic principles defined herein may be applied to some examples without departing from the spirit or scope of the disclosure. Thus, the present disclosure is not intended to be limited to the examples shown herein but is to be accorded the widest scope consistent with the following claims and the principles and novel features disclosed herein.

It should be noted that although the diagrams herein may show a specific order and composition of method blocks, it is understood that the order of these blocks may differ from what is depicted. For example, two or more blocks may be performed concurrently or with partial concurrence. Also, some method blocks that are performed as discrete blocks may be combined, blocks being performed as a combined block may be separated into discrete blocks, the sequence of certain processes may be reversed or otherwise varied, and the nature or number of discrete processes may be altered or varied. The order or sequence of any element or apparatus may be varied or substituted according to alternative arrangements. Accordingly, all such modifications are intended to be included within the scope of the present disclosure as defined in the appended claims. Such variations will depend on the machine-readable media and hardware systems chosen and on designer choice. It is understood that all such variations are within the scope of the disclosure. Likewise, software and web arrangements of the present disclosure could be accomplished with standard programming techniques with rule based logic and other logic to accomplish the various database searching blocks, correlation blocks, comparison blocks, and decision blocks.

What is claimed is:

1. A method for assessing signal quality of a signal from a subject, comprising:
    determining a signal quality assessment (SQA) value associated with an SQA metric of the signal of the subject based on at least one energy function of the signal, wherein the at least one energy function comprises a plurality of energy functions and each of the plurality of energy functions calculates a different parameter of the signal;
    receiving user input corresponding to at least one medical condition;
    selecting one or more of the plurality of energy functions based on the user input;
    determining the SQA value of the SQA metric based on the selected one or more of the plurality of energy functions;
    determining whether the SQA value of the SQA metric is above a threshold; and
    in response to determining that the SQA value of the SQA metric is above the threshold, performing additional signal processing of the signal.

2. The method of claim 1, wherein the signal comprises an ultrasound signal.

3. The method of claim 1, wherein the signal comprises one or more cerebral blood flow velocity (CBFV) waveforms.

4. The method of claim 1, further comprising
moving a probe to a first location of the subject; and
receiving, by the probe, the signal from the subject at the first location.

5. The method of claim 4, wherein the first location is at a temporal area of the subject.

6. The method of claim 4, further comprising:
determining that the SQA value of the SQA metric is not above the threshold; and
moving the probe to a second location of the subject in response to determining that the SQA value of the SQA metric is not above the threshold; and
configuring the probe to receive an additional signal of the second location.

7. The method of claim 4, further comprising:
determining that a segment of a first trajectory path of the probe has deteriorating signal quality based on the SQA value of the SQA metric for the segment, wherein the first location is on the first trajectory path; and
moving the probe along a second trajectory path different from the first trajectory path in response to determining that the segment of the first trajectory path has the deteriorating signal quality.

8. The method of claim 1, further comprising receiving the signal from a signal database, wherein performing the additional signal processing of the signal comprises at least one of:
admitting the signal as a part of a training data set or a testing data set for machine learning algorithms;
admitting the signal for testing and training improved diagnostic settings; or
admitting the signal for determining improved search algorithms.

9. The method of claim 8, further comprising disregarding the signal responsive to determining that the SQA value of the SQA metric is not above the threshold.

10. The method of claim 1, wherein the at least one energy function comprises an M-Mode energy function that calculates M-Mode energy of the signal.

11. The method of claim 10, wherein
receiving the signal comprises receiving the signal in an M-Mode; and
the M-Mode energy is determined using the signal received in the M-Mode.

12. The method of claim 1, wherein the at least one energy function comprises an envelope energy function that calculates an envelope energy parameter that is based on smoothness or velocity range of the signal.

13. The method of claim 12, wherein the envelope energy function is determined based on a spectrogram of the signal.

14. The method of claim 1, wherein the at least one energy function comprises a bounded spectral power (BSP) energy function that calculates how much velocity of the signal is near a peak velocity of the signal.

15. The method of claim 14, wherein the BSP energy function is determined based on a spectrogram of the signal.

16. The method of claim 1, wherein the at least one energy function comprises a High Frequency Ratio (HFR) energy function that calculates a ratio between power of the signal within a frequency band to power of the signal outside of the frequency band.

17. The method of claim 1, wherein the at least one energy function comprises a pulsatility index (PI) function that calculates pulsatility of the signal.

18. The method of claim 1, wherein the SQA metric is determined based on at least one of M-Mode energy, envelope energy that is based on smoothness or velocity range of the signal, bounded spectral power (BSP) energy that is based on how much velocity of the signal is near a peak velocity of the signal, or High Frequency Ratio (HFR) energy that is based on a ratio between power of the signal within a frequency band to power of the signal outside of the frequency band.

19. The method of claim 1, wherein the threshold is set based on demographic information of the subject.

20. The method of claim 1, wherein the threshold is dynamic.

21. The method of claim 20, wherein the threshold changes over time.

22. The method of claim 20, wherein
the threshold starts from an initial value;
the threshold increases from the initial value responsive to determining that the initial value is exceeded by the SQA value of the SQA metric; and
the threshold decreases from the initial value responsive to determining that the initial value is not exceeded by the SQA value of the SQA metric for a period of time.

23. The method of claim 1, further comprising determining the SQA value of the SQA metric by applying a gating function to the at least one energy function of the signal.

24. The method of claim 23, wherein the gating function comprises M-Mode energy.

25. The method of claim 1, further comprising determining the SQA metric by weighting each of the at least one energy function by applying a scalar to each of the at least one energy function of the signal.

26. The method of claim 1, wherein performing the additional signal processing of the signal comprises at least one of:
performing beat segmentation for the signal;
identifying one or more morphological features of the signal; or
displaying the one or more morphological features.

27. The method of claim 1, displaying the SQA value of the SQA metric at a display device.

28. A tool for assessing signal quality of a signal from a subject, comprising:
a processing circuit configured to:
determine a signal quality assessment (SQA) value associated with an SQA metric for a signal of the subject based on at least one energy function of the signal, wherein the at least one energy function comprises a plurality of energy functions and each of the plurality of energy functions calculates a different parameter of the signal;
receive user input corresponding to at least one medical condition;
select one or more of the plurality of energy functions based on the user input;
determine the SQA value of the SQA metric based on the selected one or more of the plurality of energy functions;
determine whether the SQA value of the SQA metric is above a threshold; and
in response to determining that the SQA value of the SQA metric is above the threshold, perform additional signal processing of the signal.

29. A non-transitory computer-readable medium having computer-readable instructions such that, when executed by a processor, assess signal quality of a signal from a subject by:
- determining a signal quality assessment (SQA) value associated with an SQA metric for the signal of the subject based on at least one energy function of the signal, wherein the at least one energy function comprises a plurality of energy functions and each of the plurality of energy functions calculates a different parameter of the signal;
- receiving user input corresponding to at least one medical condition;
- selecting one or more of the plurality of energy functions based on the user input;
- determining the SQA value of the SQA metric based on the selected one or more of the plurality of energy functions;
- determining whether the SQA value of the SQA metric is above a threshold; and
- in response to determining that the SQA value of the SQA metric is above the threshold, performing additional signal processing of the signal.

* * * * *